US00PP31967P2

(12) United States Plant Patent
Malinowski et al.

(10) Patent No.: US PP31,967 P2
(45) Date of Patent: Jul. 14, 2020

(54) ***HIBISCUS* PLANT NAMED '15353-2N'**

(50) Latin Name: ***Hibiscus* hybrid (L.)**
Varietal Denomination: 15353-2N

(71) Applicant: The Texas A&M University System, College Station, TX (US)

(72) Inventors: Dariusz P. Malinowski, Vernon, TX (US); William E. Pinchak, Vernon, TX (US); R. Steve Brown, Vernon, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 16/501,693

(22) Filed: May 22, 2019

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

(56) References Cited

U.S. PATENT DOCUMENTS

PP24,079 P3 12/2013 Hurd

OTHER PUBLICATIONS

U.S. Appl. No. 16/501,691, filed May 22, 2019, Malinowski et al.
U.S. Appl. No. 16/501,696, filed May 22, 2019, Malinowski et al.
U.S. Appl. No. 16/501,694, filed May 22, 2019, Malinowski et al.
U.S. Appl. No. 16/501,698, filed May 22, 2019, Malinowski et al.
U.S. Appl. No. 16/501,695, filed May 22, 2019, Malinowski et al.
U.S. Appl. No. 16/501,692, filed May 22, 2019, Malinowski et al.
U.S. Appl. No. 16/501,697, filed May 22, 2019, Malinowski et al.

*Primary Examiner* — Keith O. Robinson
(74) *Attorney, Agent, or Firm* — Dentons US LLP

(57) ABSTRACT

'15353-2N' is a new and distinct hardy herbaceous *Hibiscus* hybrid with novel characteristics that include upright branched stems, numerous, outward-facing, near deep pink, also referred to as folly red, flowers with dark red veins and a center eye that is between moderate brown and grayish brown, a prolonged blooming season, and hastate leaves with slightly indented margins.

3 Drawing Sheets

Latin name of the genus and species of the plant claimed: *Hibiscus* hybrid (L.).

Cultivar denomination: '15353-2N'.

BACKGROUND OF THE INVENTION

The invention relates to the new and distinct *hibiscus* plant '15353-2N'. '15353-2N' was generated from a cross performed on Jul. 26, 2014 near Vernon, Tex. between '11301-2' (pod parent, unpatented) and '13028-2' (pollen parent, unpatented). The pedigrees of each parent reflect a complex mixture of *hibiscus* species that include, for example, *H. mocheutos, H. coccineus, H. militaris*, or *H. dasycalyx*. The seed from this cross was harvested on Sep. 3, 2014 and the '15353-2N' seedling was selected in the summer of 2015. '15353-2N' was first asexually propagated near Vernon, Tex. in 2016 by stem tip cuttings. The resulting as well as subsequent asexually propagated plants have been stable and true to type throughout successive generations.

SUMMARY OF THE INVENTION

'15353-2N' differs from its parents and all other known hardy herbaceous *hibiscus* plants. The following are the most outstanding and distinguishing characteristics of '15353-2N': (1) it is a hardy perennial with dense branching and a compact growth habit; (2) it blooms profusely over a prolonged season; and (3) its flowers exhibit a near deep pink (between RHS 48A and RHS 50B) background and a center eye that is between moderate brown (RHS 165A) and grayish brown (RHS 166A).

'15353-2N' plants can be readily and unambiguously distinguished from those of its parents. '15353-2N' plants exhibit near deep pink (between RHS 48A and RHS 50B) flowers that have an average diameter of 17 cm, hastate leaves with slightly indented margins, and a compact growth habit. Whereas, '11301-2' plants (pod parent) exhibit near white (lighter than yellowish white RHS 155D) flowers with a pale pink (RHS 49D) tint that have an average diameter of 18 cm, lobed leaves with slightly indented margins, and an open bush growth habit; and '13028-2' plants (pollen parent) exhibit deep purplish red (RHS 187D) flowers that have an average diameter of 12.5 cm, hastate leaves with slightly indented margins, and a relatively compact growth habit.

'Midnight Marvel' (U.S. Pat. No. 24,079) is the *hibiscus* plant that exhibits flowers that are colored most similarly to those of '15353-2N'. Nonetheless, plants of '15353-2N' and 'Midnight Marvel' can also be readily and unambiguously distinguished at least based upon flower shape, flowering time, and flowering amount. The flowers of '15353-2N' exhibit petals that are curved such that they give the impression of being full or double flowers; whereas flowers of 'Midnight Marvel' exhibit petals that are not curved and have a flat surface. Also, plants of '15353-2N' display earlier and more profuse flowering than plants of 'Midnight Marvel'.

BRIEF DESCRIPTION OF THE DRAWINGS

'15353-2N' is illustrated by the accompanying photographs, which show the plant's form, foliage, flowers, and leaves. The colors shown are as true as can be reasonably obtained by conventional photographic procedures.

DETAILED BOTANICAL DESCRIPTION

Figure 1:
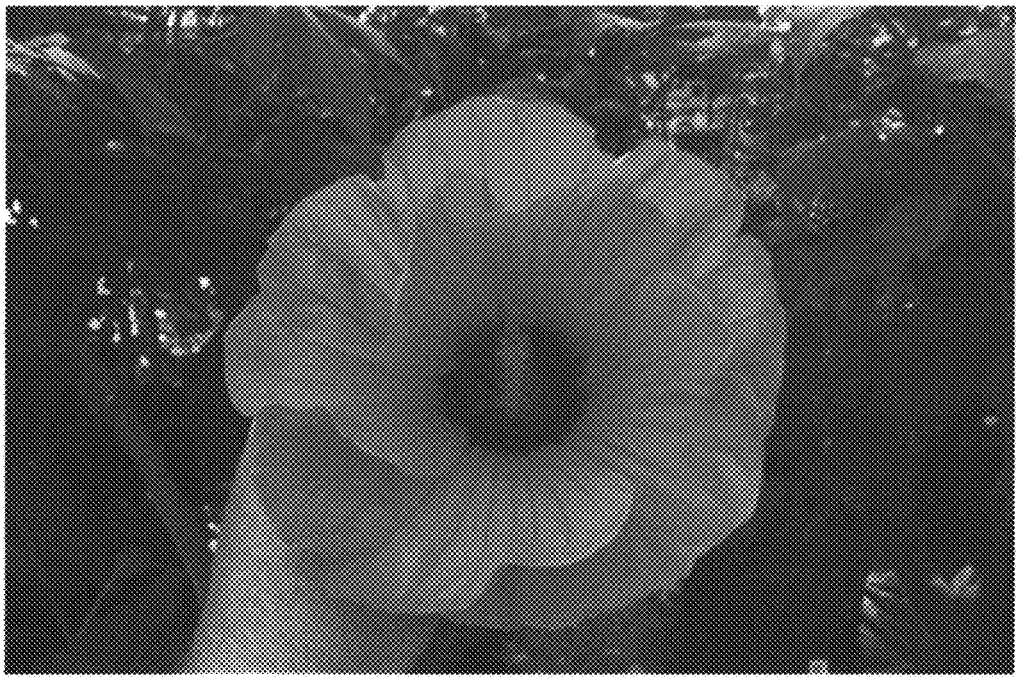
FIG. 1—Shows a '15353-2N' flower as seen looking directly at the adaxial surface of the petals on a 2-year-old plant.
Figure 2:
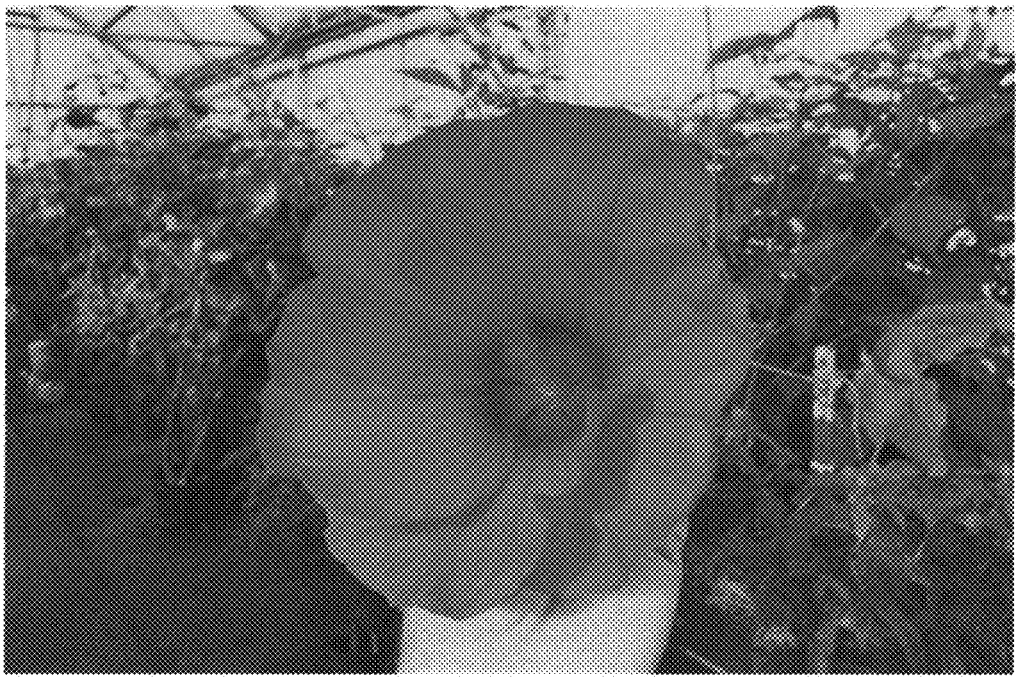
FIG. 2—Shows a '15353-2N' flower as seen looking slightly askew from the adaxial surface of the petals on a 2-year old plant.
Figure 3:
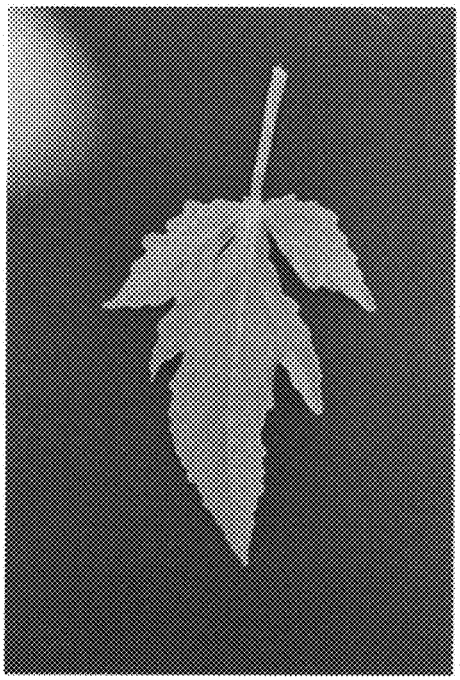
FIG. 3—Shows a '15353-2N' leaf.

The following detailed description sets forth the distinctive characteristics of '15353-2N'. The detailed description was obtained using two-year-old plants grown in loamy sand, open-field, full sun trials at a nursery near Vernon, Tex., during which the plants were supplemented with fertilizer and water as needed. These plants are natural habit and were not treated with plant growth regulators and they were not pinched at any time in the growth year. '15353-2N' has not been observed under all possible environments, and certain characteristics may vary slightly under different environmental conditions. Color references are to The Royal Horticultural Society Colour Chart of The Royal Horticultural Society of London (R.H.S.), 2001 ($4^{th}$ edition).

Propagation:

*Method.*—Stem cuttings.

*Time to initiate roots from stem cuttings after treating cuttings with a commercial rooting hormone.*—About 2 weeks under misting and at an air temperature of 85° C.

*Rooting habit.*—Normal, branching, fleshy, and developing a thick diameter (to about 2.5 cm).

*Root color.*—Pale yellow (between RHS 161D and RHS 162D), depending on soil type.

*Crop time (under normal summer growing conditions and when grown in a 4 l container from a rooted cutting).*—8 to 10 weeks to flower with very good plant vigor.

Plant:

*Plant shape and habit.*—Hardy herbaceous perennial with 6 to 8 thick upright and heavily branched main stems producing an upright spreading mound about 100 cm tall and 95 cm wide, which is widest about 50 cm above the soil line.

*Primary branches.*—8 to 16 per main stem that protrude at about a 45° angle from horizontal.

*Lateral branches.*—On the middle half of the primary stems.

*Lateral branch size.*—Between 15 cm and 30 cm long (shorter at the upper nodes) and with an average diameter of 8.0 mm at their base.

*Flower location.*—Upper ⅓ of the plant beginning at axillary nodes while still developing at the apex.

*Stem.*—Rounded, glabrous, glaucous; averages about 100.0 cm tall and 3.5 cm diameter at their base.

*Stem color.*—Between brilliant yellowish green (RHS 134C) and strong yellowish green (RHS 135C).

*Internode.*—About 18 nodes per stem below flower and about 32 total, average internode length is about 4.5 cm of unpinched plant, but varies between 2.0 to 6.0 cm and are widest in middle portion of stem.

Foliage:

*Shape.*—Hastate with slightly indented margins.

*Texture.*—Adaxial and abaxial matte.

*Leaf blade size.*—To about 15.0 cm long and 7.0 cm wide, larger proximally and becoming smaller in distal portion of stem.

*Foliage color.*—Adaxial and abaxial strong yellowish green (RHS 135C).

*Veins.*—Palmate; adaxial and abaxial veins moderate yellowish green (RHS 139D).

*Petiole size (average).*—7.0 cm long and 5.0 mm wide.

*Petiole color.*—Nearest greenish reddish orange (RHS 174C).

Flowers:

*Buds.*—One day prior to opening about 3.5 cm long and 2.5 cm in diameter, pointed apex and bluntly rounded base; and, prior to showing petals, about 3.5 cm long and 2.5 cm in diameter, ovoid with acute apex.

*Bud color.*—Exposed petal deep pink (between RHS 48A and RHS 50B).

*Epicalyx.*—Entire, smooth, puberulent both surfaces, linear with sharply acute apex and attenuate base, curved around sepals; typically 8 to 12 per flower; about 2.5 cm long tapering to base of about 3.0 mm wide.

*Epicalyx color.*—Adaxial and abaxial strong yellowish green (RHS 135C).

*Sepals.*—5, proximal half connate forming campanulate star-shaped calyx; acute apex; margin entire, edentate; puberulent abaxial glabrous adaxial; individually about 3.5 cm long and about 2.5 cm wide at fusion point. From the upper side of the flower, sepals are not visible as a star shape in the center of the flower.

*Sepal color.*—Abaxial and adaxial color strong yellowish green (RHS 135C).

*Flowers.*—Solitary, about 20 to 30 per main stem without pinching; primarily outwardly facing; average 17 cm across, larger in early part of flowering season; persist for one to two days, depending on temperature; effective for at least 14 weeks beginning early July and lasting into October (north Texas), no detectable fragrance.

*Petals.*—5; glabrous, moderately lustrous both front and back, adnate to the androecium to form a column, imbricate to about 50% overlapping at widest part (petals about 100% overlapping the next petal to either side), wavy and curved on one side making an impression of a full or double flower. Veins: Parallel branching into secondary veins in the upper part of the petal, dark red (RHS 187C); veins extend from the eye zone. Shape: Rounded. Margins: Entire, edentate. Apex: Rounded. Base: Short claw-like. Surface: Adaxial and abaxial glabrous, very slightly ribbed. Size (average): About 8.5 cm long and about 8.5 cm wide at widest portion (largest in earlier part of flowering season); center brown eye about 4.0 cm diameter. Color: Adaxial and abaxial near deep pink (between RHS 48A and RHS 50B), center eye between moderate brown (RHS 165A) and grayish brown (RHS 166A).

*Gynoecium*.—Style: Enclosed in column about 5.5 cm long and 0.5 cm wide at base; column color deep pink between (RHS 48A) and (RHS 50B); style protruding from column and split in distal 10.0 mm portion into typically 5 branches, branch diameter 2.0 mm; branch color nearest strong red (RHS 46A). Stigma: Typically 5; globose, puberulose, about 3.0 mm in diameter; color nearest strong red (RHS 46A). Ovary: Superior, about 6.5 mm across at base and 6.0 mm tall; acute apex.

*Androecium*.—Filaments: Numerous, about 140; less than 1.0 mm in diameter and about 5.0 mm long; attached along nearly the entire length of column; color nearest moderate pink (RHS 49B). Anthers: Reniform; about 2 mm long and 1 mm wide; nearest strong red (RHS 46A). Pollen: Numerous, globose, less than 0.1mm long; color strong red (RHS 46A).

*Pedicel*.—Rounded in cross section, finely puberulent; length from base of sepal to abscission point average 1.5 cm long and 4.0 mm wide, longer on early flowers decreasing in later flowers; color brilliant yellowish green (RHS 135C).

*Peduncle*.—Rounded, puberulent, average about 2.5 cm long from abscission point to stem and 4.0 mm wide, slightly longer on earlier flowers.

*Peduncle color*.—Brilliant yellowish green (RHS 135C).

*Fruit*.—Few, loculicidal capsule; glabrous; globose, occasionally with abruptly acute apex; color between light yellowish brown (RHS 199C) and dark grayish yellow (RHS 199D) when mature.

*Seed*.—Minutely floccose, typically globose; about 3.0 mm in diameter; color between dark grayish reddish brown (RHS 200A) and moderate brown (RHS 200C).

Resistance: The plant grows best with plenty of moisture, but is able to tolerate some drought once established. Other pest and disease resistance beyond that of other hardy perennial *hibiscus* cultivars has not been observed. Hardiness at least from USDA Zone 4 through 9.

Commercial use: Suitable for potted plant culture, landscaping as a specimen or en masse, and especially suited for patios and confined spaces because of the compact habit.

What is claimed is:

1. A new and distinct *Hibiscus* hybrid (L.) plant named '15353-2N' as shown and described herein.

* * * * *